United States Patent [19]

Wang

[11] Patent Number: 4,968,811

[45] Date of Patent: Nov. 6, 1990

[54] ALKENYLPHENOL DERIVATIVES

[75] Inventor: Pen C. Wang, Houston, Tex.

[73] Assignee: Shell Oil Company, Houston, Tex.

[21] Appl. No.: 356,157

[22] Filed: May 24, 1989

Related U.S. Application Data

[63] Continuation-in-part of Ser. No. 314,520, Feb. 23, 1989, Pat. No. 4,886,863.

[51] Int. Cl.$^5$ .................. C07D 481/10; C07D 471/22; C07D 495/22; C07D 493/22
[52] U.S. Cl. .................................. 548/410; 546/15; 544/6; 544/70; 544/230
[58] Field of Search ...................... 548/410; 544/6, 70; 546/15

[56] References Cited

U.S. PATENT DOCUMENTS 1,999,181  4/1935  Conover et al. ............... 260/64
4,100,140  7/1978  Zahir et al. .................... 526/90

OTHER PUBLICATIONS

Cava et al., *J. Amer. Chem. Soc.*, 79, pp. 1706–1709, (1956).
Cava et al., *J. Amer. Chem. Soc.*, 77, pp. 6022–6026, (1955).

*Primary Examiner*—Mark L. Berch

[57] ABSTRACT

Novel 1,6-diaza[4.4]spirodilactams having a hydroxyaryl substituent on each spiro ring nitrogen atom and at least one alkenyl group located on an aromatic ring carbon atom which is ortho to the hydroxy of the hydroxyaryl substituents are produced by Claisen Rearrangement of an alkenyl ether of the hydroxyaryl-substituted spirodilactam having one fewer ortho-alkenyl substituent.

14 Claims, No Drawings

ALKENYLPHENOL DERIVATIVES

RELATED APPLICATION

This application is a continuation-in-part of copending U.S. patent application Serial No. 314,520, filed February 23, 1989, now U.S. Pat. No. 4,886,863.

FIELD OF THE INVENTION

This invention relates to a novel class of spirodilactam derivatives. More particularly, the invention relates to 1,6-diaza[4.4]spirodilactams having a hydroxyaryl-containing substituent on each spiro ring nitrogen atom, wherein the hydroxyaryl substituent contains an unsaturated group in at least one aryl ring position ortho to the hydroxyl group.

BACKGROUND OF THE INVENTION

Unsaturated derivatives of polyhydric phenols are a well known class of compounds that can be cured or crosslinked to produce insoluble products that typically exhibit good solvent resistance and mechanical properties as well as relatively high heat distortion temperatures. Such unsaturated derivatives are crosslinked by reaction with catalytic or polyfunctional stoichiometric curing agents to produce tough, heat resistant products which are processed by conventional methods into films or laminates with fiber glass or other reinforcements or into shaped objects and the crosslinked products are additionally useful in adhesive formulations.

When the unsaturated phenolic derivative is an ether of a polyhydric phenol, or is produced from a polyhydric phenol, much of the technology is broadly conventional. The phenolic ether is suitably cured or crosslinked as such but additionally the ether is rearranged to produce a phenol having an unsaturated ortho substituent (occasionally para), which phenol is also curable. The disclosure of Zahir, U.S. 4,100,140, is illustrative. The compound 2,2-di(4-hydroxyphenyl)propane, also known as bisphenol A or BPA, is converted to its sodium salt and reacted with allyl chloride to produce the diallyl ether of BPA, i.e., 2,2-di(4-allyloxyphenyl) propane. This diallyl ether is curable, for example, by heating the diallyl ether with an imide-containing curing agent. Alternatively, the diallyl ether is subjected to rearrangement according to the classical Claisen Rearrangement to produce the corresponding ortho-allylphenol, i.e., 2,2-di(4-hydroxy-3-allylphenyl)propane. The ortho allyl derivative is also curable as by heating with a bis(maleimide). It is also known to produce an allyl ether of the ortho-allylphenol and subsequently conduct a second rearrangement to produce an o,o-diallylphenol derivative. To obtain even greater functionality, an allyl ether of the diallylphenol is produced, all by conventional technology.

On some occasions, the cured products which provide the more desirable properties, particularly in high temperature applications, are those wherein the phenolic derivatives are of polycyclic structure. It would be of advantage to provide a novel class of unsaturated derivatives of phenols having a plurality of rings within the molecular structure.

SUMMARY OF THE INVENTION

The present invention provides a novel class of spirodilactam compounds having phenolic substituents which incorporate unsaturated groups as phenolic ring substituents. More particularly, the invention relates to 1,6-diaza [4.4]spirodilactam compounds having a hydroxyaryl substituent on each spiro ring nitrogen atom, the hydroxyaryl substituent being substituted in at least one aromatic ring position ortho relative to the hydroxyl with an alkenyl group.

DESCRIPTION OF THE INVENTION

The novel spirodilactam derivatives of the invention are hydroxyaryl-substituted 1,6-diaza [4.4]spirodilactams wherein the aryl aromatic ring is substituted in at least one ring position ortho relative to the hydroxyl with an alkenyl group. Although a wide variety of substituted spirodilactam derivatives having a variety of additional substituents are contemplated by the invention, a preferred class of such spirodilactams comprises spirodilactam derivatives of up to 60 carbon atoms represented by the formula

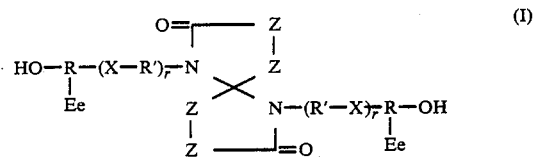

wherein R independently is aromatic of up to 15 carbon atoms and up to two ' independently is R or aliphatic or up to 10 aromatic rings, inclusive, R carbon atoms inclusive, r independently is 0 or 1, X independently is a direct valence bond, alkylene of up to 8 carbon atoms inclusive, oxy, thio, sulfonyl, carbonyl, dioxyphenylene, 2,2-di(oxyphenyl)propane, di(oxyphenyl)sulfone or dioxydiphenylene, Z independently is >C(Z')$_2$ in which Z independently is hydrogen, lower alkyl, preferably methyl, halo, preferably the lower halogen fluoro or chloro, or aryl, preferably phenyl, or Z is such that two adjacent Z groups taken together form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z , two of which form a bridge between the carbon atoms connected by the adjacent Z groups, E independently is 2-alkenyl of up to 8 carbon atoms inclusive located on an aromatic ring carbon atom ortho to the indicated hydroxyl group and e independently is 1 or 2. In the above formula I, R and R' are hydrocarbyl, that is contain only atoms of carbon and hydrogen or are substituted hydrocarbyl containing additional atoms in the form of inert monovalent substituents on carbon atoms, for example, halo, preferably the middle halogens chloro or bromo.

In the embodiment of the above formula wherein the Z moieties are not part of a fused ring substituent and are therefore acyclic, i.e., Z is >C(Z')$_2$, illustrative ortho-alkenyl hydroxyaryl-substituted spirodilactam products include 1,6-di(4-hydroxy-3-allylphenyl)-1,6-diazaspiro4.4]nonane-2,7-dione, 1,6-di(3-hydroxy-4-allyl-5-chlorophenyl)-3,8-dimethyl-1,6-diazaspiro[4.4]nonane-2,7-dione, 1,6-di[4-(4-hydroxy-3-allylbenzoyl)phenyl]-3-phenyl-1, 6-diazaspiro[4.4]nonane-2,7-dione, 1,6-di(4-hydroxy-3,5-diallylphenyl)-3,3,4,4,8,8,9,9-octamethyl-1,6-di(4-hydroxy-3-methallylphenyl)-1,6-diazaspiro[4.4]nonane-2,7-dione, 1,6-di[4-(4-hydroxy-3-crotylbiphenyl)]-3,3-dimethyl-1,6-diazaspiro[4.4]- nonane-2,7-dione, 1,6-di[2-(4-hydroxy-3-methallylphenyl)propyl]-1,6-diazaspiro[4.4]nonane- 2,7-dione, 1,6-di[4-(4-hydroxy-3-allylphenylisopropyl)-phenyl].1,6-diazaspiro[4.4]nonane-2,7-dione and 1,6-di[4-hydroxy-3-(2hexenyl) phenyl[-3,4,8,9-tetrafluoro-1,6-diazaspiro[4.4nonane-2,7-dione. In the embodiment of the spirodilactam derivatives of formula I wherein the adjacent Z moieties of each spiro ring form a cyclic, fused ring substituent, i.e., the adjacent Z groups are Z.., illustrative spirodilactam derivatives include 1,6-di(4-hydroxy-3,5-diallylphenyl)-3,4,8,9-dibenzo1,6-diazaspiro[4.4]nonane-2,7-dione, 1,6-di[4-(4-hydroxy-3-methallylphenyloxy)phenyl]-3,4,8,9-di(pyrido)-1,6-diazaspiro[4.4]nonane-2,7-dione and 1,6-di[4-(4-hydroxy-3-allylphenylthio)phenyl]-3,4,8,9-di(cyclopentano)-1,6-diazaspiro [4.4]nonane-2,7-dione. Also suitable are those substituted spirodilactam derivatives wherein one spiro ring has a cyclic fused ring substituent and one spiro ring is free of fused ring substituents, e.g., 1,6-di(4-hydroxy-3-allyphenyl)-3,4-benzo-8-methyl-1,6-diazaspiro[4.4]nonane 2,7-dione and 1,6-di[1-(4-hydroxy-3-allylnaphthyl)]-3,4-cyclohexano-1,6-diazaspiro [4.4]nonane-2,7-dione.

In general, the spirodilactam derivatives of the above formula I wherein E is allyl and e is 1 are preferred, as are the compounds wherein R and R are aromatic and hydrocarbyl. Further preferred are those derivatives wherein each r is 0 and R has a single aromatic ring, i.e., R is phenylene. Within the spirodilactam ring portion of the molecule, spirodilactam derivatives free from fused ring substituents, i.e., Z is >C(Z')₂, are preferred as are the derivatives in which both spiro rings incorporate a fused ring substituent. The compound 1,6-di(4-hydroxy-3-allylphenyl) -1,6-diazaspiro4.4nonane-2,7-dione is an especially preferred member of the former class whereas 1,6-di(4-hydroxy-3-allylphenyl)-3,4,8,9-dibenzo-1,6-diazaspiro [4.4]nonane-2,7-dione is an especially preferred member of the latter class.

The ortho-alkenyl hydroxyaryl-substituted sprirodilactams are produced by thermal rearrangement of a alkenyl ether of the corresponding hydroxyaryl-substituent spirodilactam. In terms of the ortho-alkenyl derivatives of formula I, the alkenyl ethers are represented by the formula

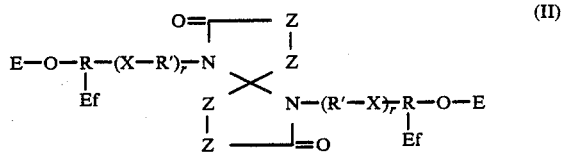

wherein R, R', r, X, Z and E have the previously stated meanings and f is (e−1), that is, f is 0 or Rearrangement of these alkenyl ethers (formula II) to the corresponding ortho-alkenyl hydroxy compound (formula VI) is by the well-known Claisen Rearrangement. In this process, the alkenyl ether is dissolved in a suitable reaction diluent and the resulting mixture is heated, in a liquid phase, until reaction is complete. Reaction diluents that are satisfactory in the rearrangement process are capable of dissolving at least a portion of the alkenyl ether reactant and are inert to the reactant and ortho-alkenyl hydroxy compound product. Such diluents include ethers, for example acyclic ethers such as diethylene glycol diethyl ether and tetraethylene glycol dimethyl ether as well as cyclic ethers such as tetrahydrofuran and dioxane, N-alkylamide diluents such as N,N-dimethylacetamide, N,N-dimethylformamide and N-methyl-2-pyrrolidone, and sulfur-containing diluents such as dimethyl sulfoxide and sulfolane. The temperature of the rearrangement reaction is typically from about 150° C. to about 300° C., preferably from about 175° C. to about 250° C., depending in part on the particular ether to be rearranged, and a suitable reaction pressure is sufficient to maintain the reaction mixture in a liquid phase. Such pressures are from about 1 atmosphere to about 20 atmospheres. Subsequent to rearrangement the resulting ortho-alkenyl hydroxyaryl-substituted spirodilactam product is recovered by conventional methods such as extraction, solvent removal or precipitation.

Thus, the production of the ortho-alkenyl hydroxy compounds is by way of a sequential two-step process. Initially an alkenyl ether of the hydroxyaryl-substituted spirodilactam is produced by conversion of the hydroxy compound to a metal salt, preferably an alkali metal salt such as the sodium or potassium salt, and reaction of the salt with an alkenyl halide, e.g., allyl chloride or bromide. The alkenyl ether, in a second step, is rearranged according to the process of the invention to produce the ortho-alkenyl hydroxy compound. If the introduction of a second orthoalkenyl substituent is desired, as in compounds of formula I wherein e is 2, the process is repeated to form an alkenyl ether of the ortho-alkenyl hydroxy compound which is subsequently rearranged to the ortho, orthodi (alkenyl)hydroxyaryl-substituted spirodilactam.

The hydroxyaryl-substituted spirodilactams are described and claimed in copending U.S. patent applications allowed Serial No. 172,000, filed Mar. 23, 1988, 4,889,907 and allowed and Serial No. 245,618, filed September 16, 1988U.S. Pat. No. 4,939,251. The hydroxyaryl-substituted sprirodilactam alkenyl ethers, compounds of formula II wherein f is 0, are described and claimed in copending U.S. Pat. 4,847,388, Each of these applications is incorporated herein by reference.

By way of a specific illustration of the production of compounds of the invention, 1,6-di(4-hydroxyphenyl)-1,6-diazaspiro[4.4]nonane-2,7-dione is reacted with a slight stoichiometric excess of sodium hydroxide to produce the disodium salt of 1,6-di(4-hydroxyphenyl)-1,6-diazaspiro[4.4]- nonane-2,7-dione, which salt reacts with allyl chloride to produce 1,6- [di (4-allyloxyphenyl)-1,6-diazaspiro[4.4]nonane-2,7-dione. The allyloxy compound is rearranged by application of heat to 1,6-di(4-hydroxy-3-allyl-phenyl)-1,6-diazaspiro [4.4]nonane-2,7-dione. If a di(ortho alkenyl) compound is desired, the process is repeated via the alkali metal salt intermediate to form 1,6-di(4-allyloxy-3-allylphenyl)-1,6-diazaspiro4.4- nonane-2,7-dione which undergoes Claisen Rearrangement according to the invention to yield 1,6-bis(4-hydroxy-3,5-diallylphenyl)-1,6-diazaspiro[4.4]- nonane-2,7-dione. Other specific starting materials and the products resulting therefrom will be apparent from consideration of the formulas of the ether reactant (formula II) and the ortho-alkenyl product (formula 1).

It should be appreciated, however, that the rearrangement to produce the products of the invention, like other Claisen Rearrangements, provides an ortho-alkenyl substituent which is inverted in the sequence of carbon atoms from the alkenyl moiety of the ether reactant. What was the "gamma" or third carbon atom of the alkenyl moiety of the ether becomes the carbon atom attached to the aromatic ring of the ortho-alkenyl derivative. In the case of the preferred allyl ethers, rearrangement provides an ortho-allyl derivative and inversion, although present, produces no observable difference. However, rearrangement of a crotyl ether produces a 2-(3-butenyl)-substituted product. From a straight-chain four-or-more carbon alkenyl ether is produced a branched-chain ortho-alkenyl substituent. This inversion is conventional for Claisen Rearrangements.

The ortho-alkenyl hydroxyaryl-substituted spirodilactams are normally solid at room temperature but are curable at elevated temperatures to produce cured products which exhibit good properties of toughness. Although the alkenyl derivatives are curable with a number of conventional polyfunctional curing agents such as isocyanates, a preferred loss of curing agents are the bis(maleimides), for example, di(4-maleimidophenyl)methane. Curing takes place by heating at temperatures from about 200° C. to about 300° C. and generally employs approximately equal proportions by weight of the ortho-alkenyl derivative and the bis(maleimide). The cured products are tough and show good solvent resistance. The cured products are processed by methods conventional for thermoset resins to produce coatings, adhesives and fiber-reinforced composites wherein the fibers are glass or carbon. The cured products are also useful as impregnating and casting resins.

The invention is further illustrated by the following Illustrative Embodiments which should not be construed as limiting the invention.

ILLUSTRATIVE EMBODIMENT I

To a three liter flask was charged a mixture of 202.8g (0.6 mole) of 1,6-di(4-hydroxyphenyl)-1,6-diasaspiro[4.4]nonane-2,7-dione, 91.22g (0.6 mole) of potassium carbonate, 200 ml of toluene and liter of N,N-dimethylacetamide. The mixture was heated to 150°-160°C. and water was removed by azeotropic distillation with the toluene. When the water removal was complete, the temperature was lowered to 80°-90 ° C. and 200.2g (1.2 mole) of allyl bromide in 200 ml of N,N-dimethylacetamide was added over the next 80 minutes. The reaction temperature was then raised to 90° C for 12 hours. The resulting mixture was cooled, filtered and concentrated and was then poured slowly into a mixture of hexane and ether. The precipitated product was recovered by filtration and dried in a vacuum oven at 80° C. The product had a melting point of 152° -155° C and the nuclear magnetic resonance spectra were consistent with the structure of 1,6-di(4-allyloxyphenyl)-1,6-diazaspiro [4.4]nonane-2,7-dione.

ILLUSTRATIVE EMBODIMENT II

A sample of the product of Illustrative Embodiment I was dissolved in N-methyl-2-pyrrolidone and heated at 200°-205°C. for 12 hours. The resulting product was recovered in yield of greater than 90. The a vacuum oven at 80° C. The yield was greater than 90. The melting point of the product was 237°-245 °C. and the infrared and nuclear magnetic resonance spectra were consistent with the structure of 1,6-di(4-hydroxy-3-allyphenyl) 1,6-diazaspiro[4.4]nonane-2,7-dione.

ILLUSTRATIVE EMBODIMENT III

When a sample of the product of Illustrative Embodiment II is heated with an equal proportion by weight of di(4-maleimidophenyl)methane, a tough, crosslinked product will result.

What is claimed is:

1. A spirodilactam of up to 60 carbon atoms represented by the formula

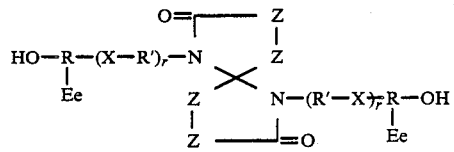

wherein R is aromatic of up to 15 carbon atoms and up to two aromatic rings, inclusive, R' is R, X is a direct valence bond, alkylene of up to 8 carbon atoms, inclusive, oxy, thio, sulfonyl, carbonyl, dioxyphenylene, 2,2-di(oxyphenyl)propane, di(oxyphenyl)sulfone or dioxydiphenylene, r is 0 or 1, Z independently is >C(Z')$_2$ in which Z independently is hydrogen, lower alkyl, fluoro, chloro- or phenyl, or Z is such that two adjacent Z groups together form a ring system Z" of from 5 to 7 ring atoms up to two of which are heteroatoms selected from nitrogen, oxygen or sulfur with the remainder of the ring atoms being carbon atoms, two carbon atoms of which form a bridge between the carbonyl and spiro ring carbon atoms connected by the two adjacent Z groups, E independently is 2-alkenyl of up to 8 carbon atoms inclusive located on an aromatic ring carbon atom located ortho to the hydroxyl group, and e independently is 1 or 2.

2. The spirodilactam of claim 1 wherein e is 1.

3. The spirodilactam of claim 2 wherein R and R' are aromatic are hydrocarbyl.

4. The spirodilactam of claim 3 wherein E is allyl.

5. The spirodilactam of claim 4 wherein r is 0.

6. The spirodilactam of claim 5 wherein Z is >C(Z')$_2$.

7. The spirodilactam of claim 6 wherein Z' is hydrogen or methyl.

8. The spirodilactam of claim 7 wherein R is phenylene.

9. The spirodilactam of claim 8 wherein Z is hydrogen.

10. The spirodilactam of claim 9 wherein R is p-phenylene.

11. The spirodilactam of claim 5 wherein adjacent Z groups are Z".

12. The spirodilactam of claim 11 wherein R is phenylene.

13. The spirodilactam of claim 12 wherein Z" is benzo.

14. The spirodilactam of claim 13 wherein R is p-phenylene.

* * * * *